United States Patent [19]

Bernstein et al.

[11] Patent Number: 4,603,131

[45] Date of Patent: Jul. 29, 1986

[54] METHOD AND COMPOSITION FOR TREATING AND PREVENTING IRRITATION OF THE MUCOUS MEMBRANES OF THE NOSE

[76] Inventors: Joel E. Bernstein, 615 Brierhill Rd., Deerfield, Ill. 60015; Clarence J. Endicott, Abbott Laboratories, North Chicago, Ill. 60064

[21] Appl. No.: 372,231

[22] Filed: Apr. 26, 1982

[51] Int. Cl.[4] ............... A61K 31/55; A61K 31/135
[52] U.S. Cl. ........................... 514/220; 514/654
[58] Field of Search .............. 424/278, 244, 330; 514/220, 654

[56] References Cited

U.S. PATENT DOCUMENTS

| | | | |
|---|---|---|---|
| 3,144,442 | 8/1964 | Schindler et al. | 260/239 |
| 3,705,942 | 12/1972 | Grunwaldt | 424/244 |
| 4,082,850 | 4/1978 | Cassman et al. | 424/278 |
| 4,370,324 | 1/1913 | Bernstein | 424/244 |

*Primary Examiner*—Leonard Schenkman
*Attorney, Agent, or Firm*—Ronald A. Sandler; Jerry A. Schulman

[57] ABSTRACT

A method and composition for preventing and treating irritation of the mucous membranes of the nose wherein a tricyclic anti-depressant topically applied to the nose is effective prophylactically to prevent irritation and a combination of the tricyclic anti-depressant with a vasoconstrictor is effective to prevent and to alleviate irritation of the mucous membranes of the nose.

24 Claims, No Drawings

METHOD AND COMPOSITION FOR TREATING AND PREVENTING IRRITATION OF THE MUCOUS MEMBRANES OF THE NOSE

BACKGROUND OF THE INVENTION

Allergic and irritant conditions of the mucous membranes of the nose are quite common and are treated with sympathomimetic amines applied locally to produce vasoconstriction of local blood vessels. Such irritation or allergies of the mucous membranes of the nose may follow introduction of foreign particles or chemical pollutants or may be part of the allergic manifestations of asthma, hayfever, and allergic rhinitis resulting in swollen mucous membranes, stuffiness and/or more or less continued discharge from the nose.

While there are a number of vasoconstrictive compounds available for treating irritation of the mucous membrane of the nose there are few effective compounds available for preventing irritation of the mucous membrane of the nose due to irritant and/or allergic conditions, that is there is no prophylactic treatment available.

We have discovered that tricyclic anti-depressants usually prescribed for ameliorating the effects of severe depression are prophylactically effective when applied topically to prevent irritation of the mucous membrane of the nose upon exposure to irritant conditions. These tricyclic anti-depressants alone have little effect on the treatment of already irritated mucous membranes, but when combined with known vasoconstrictors are effective for preventing future irritations while effectively treating present irritation.

SUMMARY OF THE INVENTION

The present invention relates to a method and composition for preventing and treating irritation of the mucous membranes of the nose.

A principal object of the present invention is to provide a method and composition for preventing irritation of a mucous membrane of the nose caused by allergies, chemical pollutants, or physical irritants manifested by sneezing, discomfort, stuffiness or mucous discharge comprising applying topically to a mucous membrane of the nose a therapeutically effective amount of a tricyclic anti-depressant of the formula:

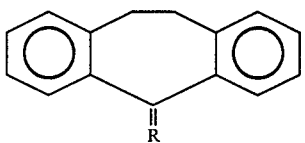

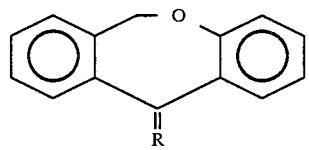

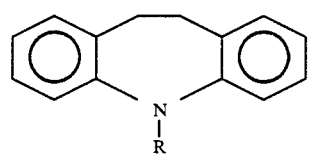

wherein R is an aliphatic secondary or tertiary amine.

Another object of the present invention is to provide a method of the type set forth wherein R is a secondary or tertiary amine connected to the ring structure by a three carbon chain.

Yet another object of the present invention is to provide a method of the type set forth wherein the tricyclic anti-depressant is selected from the group consisting of imipramine, amitriptyline, doxepin, nortriptyline, protriptyline, desipramine and the acid addition salts thereof.

A further object of the present invention is to provide a method of preventing irritation of a mucous membrane of the nose caused by allergies, chemical pollutants, or physical irritants manifested by sneezing, discomfort, stuffiness or mucous discharge comprising applying topically to a mucous membrane of the nose a therapeutically effective amount of a tricyclic anti-depressant and a vasoconstrictor wherein the tricyclic anti-depressant is selected from the group consisting of:

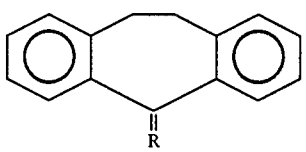

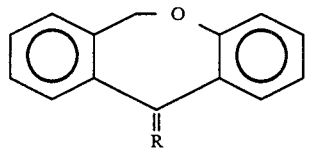

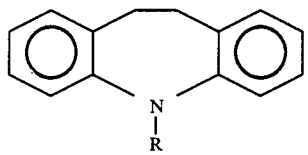

wherein R is an aliphatic secondary or tertiary amine.

Still another object of the present invention is to provide a composition for preventing irritation of a mucous membrane of the nose caused by allergies, chemical pollutants, or physical irritants manifested by sneezing, discomfort, stuffiness or mucous drainage comprising a therapeutically effective amount of a tricyclic anti-depressant selected from the group consisting of:

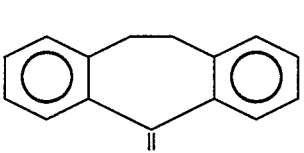

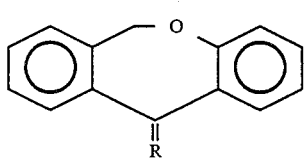

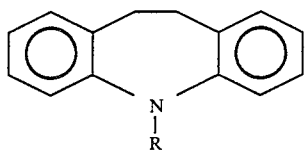

wherein R is an aliphatic secondary or tertiary amine in a suitable fluid carrier having an acceptable preservative and a buffering agent suitable to maintain the pH of the composition in the range of from about 3 to about 7, the topical application of the composition to a mucous membrane of the nose prophylactically preventing the irritation.

A still further object of the present invention is to provide a composition of the type set forth wherein the tricyclic anti-depressant is selected from the group consisting of dibenzazepine, dibenzocycloheptadiene, dibenzoxepin, and derivatives thereof.

Yet another object of the present invention is to provide a composition for preventing irritation of a mucous membrane of the nose caused by allergies, chemical pollutants, or physical irritants manifested by sneezing, discomfort, stuffiness or mucous drainage comprising a therapeutically effective amount of a tricyclic anti-depressant and a vasoconstrictor wherein the tricyclic anti-depressant is selected from the group consisting of:

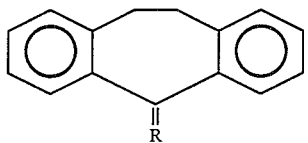

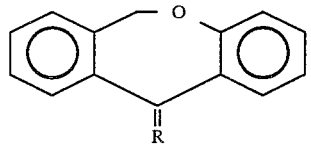

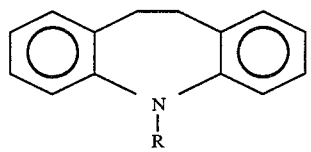

wherein R is an aliphatic secondary or tertiary amine in a suitable fluid carrier having an acceptable preservative and a buffering agent suitable to maintain the pH of said composition in the range of from about 3 to about 7.

These and other objects of the present invention will be more readily understood when considered in conjunction with the following detailed description and examples.

DESCRIPTION OF THE PREFERRED EMBODIMENTS

In the practice of this invention, nose drops are prepared employing 0.005% by weight to 1.25% by weight concentrations of the category of pharmacological agents known as the tricyclic anti-depressants, such as doxepin, amitriptyline and imipramine hydrochloride, respectively a tertiary amine derivative of dibenzoxepin, dibenzocycloheptadiene and dibenzazepine, in aqueous vehicles containing various viscosity adjusting agents, preservatives, tonicity adjusting agents, and buffering agents. Such nose drops are instilled from one to four times daily to prevent symptoms of nose irritation or allergy. Inclusion of known vasoconstrictor agents allows such drops to be used both prophylactically as well as therapeutically to relieve and prevent such nose irritation.

The preferred pH of the nose drop composition is in the range of from about 3 to about 7 and the buffering agents useful for obtaining said pH are sodium phosphate monobasic and sodium phosphate dibasic as well as citric acid, sodium citrate, acetic acid, sodium acetate, boric acid, sodium carbonate, sodium borate, hydrochloride acid and sodium hydroxide. Buffering agents may be present in the range of from about 0.1 to about 0.5% by weight of the composition but the pH is the controlled variable.

The tonicity agent is preferably sodium chloride and other pharmaceutically acceptable salts such as potassium chloride, calcium chloride, magnesium chloride and zinc sulfate. The osmotic agents such as sorbitol, dextrose and glycerin may also be used as tonicity agents. These osmotic agents also serve as humectant, emollient and flavoring agents. Certain aromatic oils may also be used as flavoring agents. The viscosity agent may be polyvinyl alcohol as well as methyl cellulose, hydroxymethyl cellulose, hydroxy propylmethyl cellulose, carboxymethyl cellulose and other soluble polymers. The viscosity adjusting agents may be present in varying ranges from about 0.5% to about 2.5% by weight of the composition. The preservatives useful in the present invention include benzalkonium chloride, edetate disodium, sodium bisulfite, phenylmercuric acetate, cetylpyridinium chloride, thimerosal, chlorobutanol, cetyltrimethyl ammonium bromide, methylparaben, propylparaben and butylparaben usually present in the range of from about 0.01% to about 0.5% by weight of the composition.

The vasoconstrictors useful in the present invention are phenylephrine hydrochloride as well as the acid addition salts of tetrahydrozoline, xylometazoline, oxymetazoline, naphazoline, phenylephrine and ephedrine. The vasoconstrictors are generally present in the range of from about 0.01% to about 1.0%, depending on the vasoconstrictor used.

Although by way of example imipramine will be used in combination with other ingredients to illustrate the compositions and methods of the present invention, both tertiary and secondary amines of the tricyclic anti-depressants are effective and are similar in their pharmacological action. The tertiary amines include amitriptyline, doxepin, and imipramine, respectively derivatives of dibenzocycloheptadiene, dibenzoxepin and dibenzazepine and have the following formulas:

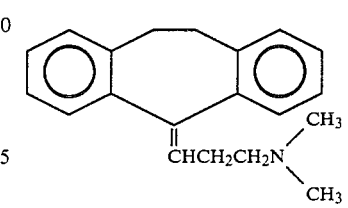

Amitriptyline

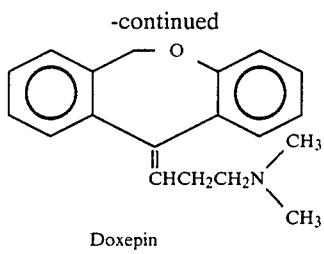

Doxepin

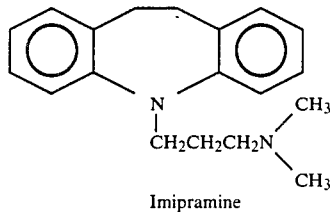

Imipramine

The secondary amines include nortriptyline, protriptyline and desipramine, respectively derivatives ot dibenzocycloheptadiene, dibenzoxepin and dibenzazepine and have the following formulas:

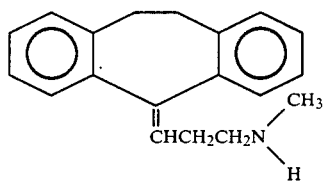

Nortriptyline

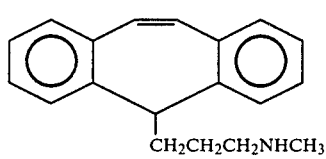

Protriptyline

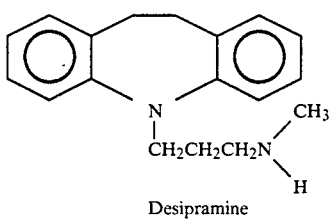

Desipramine

The following Examples of the present invention are for purposes of illustration only and are effective for the prophylactic prevention of irritation of the mucous membrane of the nose when administered topically in divided doses from 1 to 4 times per day. The tricyclic anti-depressants, when combined with an appropriate vasoconstrictor, see Example VI, are effective in treating irritated mucous membranes as well as in preventing irritation.

EXAMPLE I

A composition consists of 0.05% imipramine hydrochloride; 0.368% sodium phosphate monobasic and 0.026% sodium phosphate dibasic as buffers; 4.0% sorbitol as an osmotic agent, flavorant, humectant and emollient; 0.01% benzalkonium chloride and 0.1% edetate disodium as preservatives; and 95.446% purified water. All percents are weight percents in all Examples.

EXAMPLE II

A composition consists of 0.05% imipramine hydrochloride; 0.368% sodium phosphate monobasic and 0.026% sodium phosphate dibasic as buffers; 4.0% sorbitol as an osmotic agent, flavorant, humectant and emollient; 1.5% polyvinyl alcohol as a viscosity adjuster; 0.1% benzalkonium chloride and 0.1% sodium bisulfite as preservatives; and 93.946% purified water.

EXAMPLE III

A composition consists of 0.05% imipramine hydrochloride; 0.368% sodium phosphate monobasic and 0.026% sodium phosphate dibasic as buffers; 0.3% sodium chloride as a tonicity adjuster; 0.01% benzalkonium chloride, 0.1% edetate disodium as preservatives; and 99.146% purified water.

EXAMPLE IV

A composition consists of 0.05% imipramine hydrochloride; 0.368% sodium phosphate monobasic and 0.026% sodium phosphate dibasic as buffers; 4.0% sorbitol (osmotic agent), flavorant, humectant and emollient; 1.5% polyvinyl alcohol as a viscosity adjuster; 0.01% benzalkonium chloride, 0.1% edetate disodium and 0.1% sodium bisulfite as preservatives; 93.846% purified water.

EXAMPLE V

A composition consists of 0.05% imipramine hydrochloride; 0.368% sodium phosphate monobasic and 0.026% sodium phosphate dibasic as buffers; 4.0% sorbitol (osmotic agent), flavorant, humectant and emollient; 0.01% benzalkonium chloride and 0.1% sodium bisulfite as preservatives; and 95.446% purified water.

EXAMPLE VI

A composition consists of 0.05% imipramine hydrochloride; 0.368% sodium phosphate monobasic and 0.026% sodium phosphate dibasic as buffers; 4.0% sorbitol (osmotic agent), flavorant, humectant and emollient; 0.01% benzalkonium chloride and 0.1% edetate disodium as preservatives; 95.20% purified water; and 0.25% phenylephrine hydrochloride as a vasoconstrictor.

All compositions are prepared at room temperature by conventional mixing techniques.

What is claimed is:

1. A method of preventing irritation of a mucous membrane of the nose caused by allergies, chemical pollutants, or physical irritants manifested by sneezing, discomfort, stuffiness or mucous discharge comprising applying topically to a mucous membrane of said nose a therapeutically effective amount of a tricyclic anti-depressant selected from the group consisting of:

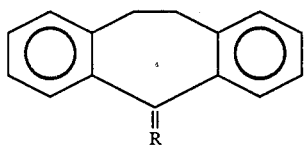

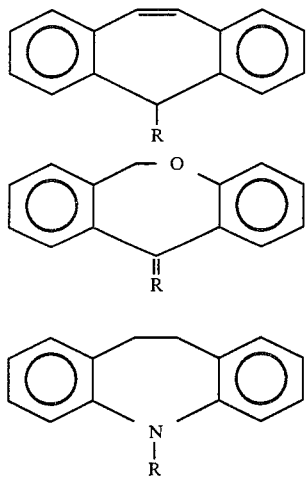

wherein R is an aliphatic secondary or tertiary amine connected to the ring by a three carbon chain.

2. The method of claim 1, wherein the tricyclic antidepressant is present in an aqueous carrier at a concentration of not less than about 0.005% by weight of the carrier.

3. The method of claim 1, wherein the tricyclic antidepressant is present in an aqueous carrier at a concentration in the range of between about 0.05% by weight and about 0.005% by weight of the carrier.

4. The method of claim 1, wherein the tricyclic antidepressant is selected from the group consisting of the acid addition salts of imipramine, amitriptyline and doxepin.

5. The method of claim 1, wherein the tricyclic antidepressant is selected from the group consisting of nortriptyline, protriptyline and desipramine.

6. A method of preventing irritation of a mucous membrane of the nose caused by allergies, chemical pollutants or physical irritants manifested by sneezing, discomfort, stuffiness or mucous discharge comprising applying topically to a mucous membrane of said nose a therapeutically effective amount of a tricyclic antidepressant selected from the group consisting of imipramine, amitriptyline, doxepin, nortriptyline, protriptyline, desipramine and the acid addition salts thereof.

7. A method of preventing irritation of a mucous membrane of the nose caused by allergies, chemical pollutants or physical irritants manifested by sneezing, discomfort, stuffiness or mucous discharge as well as treating already irritated mucous membranes comprising applying topically to a mucous membrane of said nose a therapeutically effective amount of a tricyclic anti-depressant and a vasoconstrictor wherein the tricyclic anti-depressant is selected from the group consisting of:

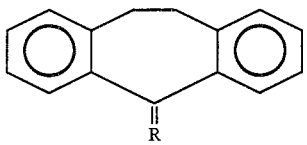

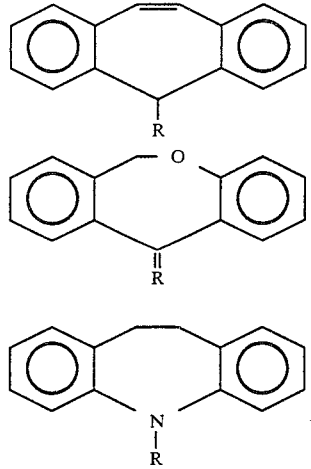

wherein R is an aliphatic secondary or tertiary amine connected to the ring by a three carbon chain.

8. The method of claim 7, wherein the tricyclic antidepressant and the vasoconstrictor are present in an aqueous carrier, the concentration of the tricyclic antidepressant in the carrier being not less than about 0.005% by weight of the carrier and the concentration of the vasoconstrictor in the carrier being not less than about 0.01% by weight of the carrier.

9. The method of claim 8, wherein the vasoconstrictor is present in the range of between about 0.01% by weight and about 1.0% by weight of the carrier.

10. The method of claim 8, wherein the anti-depressant is present in the range of between about 0.005% by weight and about 1.25% by weight of the carrier.

11. The method of claim 7, wherein the vasoconstrictor is selected from the group consisting of the acid addition salts of tetrahydrozoline, xylometazoline, oxymetazoline, phenylephrine and ephedrine.

12. The method of claim 11, and further comprising a pharmaceutically acceptable viscosity adjusting agent, a preservative, and a buffering agent, wherein the pH is maintained in the range of from about 3 to about 7.

13. The method of claim 12, wherein said vasoconstrictor is selected from the group consisting of phenylephrine hydrochloride, tetrahydrozoline hydrochloride, xylometazoline hydrochloride, oxymetazoline hydrochloride, naphazoline hydrochloride, phenylephrine hydrochloride and ephedrine hydrochloride; wherein the viscosity adjusting agent is selected from the group consisting of polyvinyl alcohol, methyl cellulose, hydroxymethyl cellulose, hydroxy propylmethyl cellulose, carboxymethyl cellulose and other soluble polymers; the preservative is selected from the group consisting of benzalkonium chloride, edetate disodium, sodium bisulfite, phenylmercuric acetate, cetylpyridinium chloride, thimerosal, chlorobutanol, cetyltrimethyl ammonium bromide, methylparaben, propylparaben and butylparaben; the buffering agent is selected from the group consisting of sodium phosphate monobasic, sodium phosphate dibasic, citric acid, sodium citrate, acetic acid, sodium acetate, boric acid, sodium carbonate, sodium borate, hydrochloric acid and sodium hydroxide.

14. A composition for preventing irritation of a mucous membrane of the nose cause by allergies, chemical pollutants, or physical irritants manifested by sneezing, discomfort, stuffiness or mucous drainage comprising a therapeutically effective amount of a tricyclic anti-depressant selected from the group consisting of:

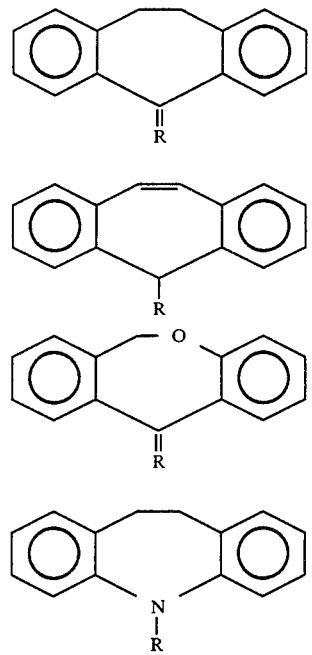

wherein R is an aliphatic secondary or tertiary amine connected to the ring by a three carbon chain in a suitable nasal fluid carrier having an acceptable preservative and a buffering agent suitable to maintain the pH of said composition in the range of from about 3 to about 7, and a flavoring agent the topical application of said composition being suitable for administration to a mucous membrane of the nose prophylactically preventing said irritation.

15. The composition of claim 14, wherein the tricyclic anti-depressant is present in an aqueous carrier at a concentration of not less than about 0.005% by weight of the carrier.

16. The composition of claim 14, wherein the tricyclic anti-depressant is present in an aqueous carrier at a concentration in the range of between about 0.005% by weight and about 1.25% by weight of the carrier.

17. The composition of claim 14, wherein the tricyclic anti-depressant is selected from the group consisting of the acid addition salts of imipramine, amitriptyline and doxepin.

18. The composition of claim 14, wherein the tricyclic anti-depressant is selected from the group consisting of nortriptyline, protriptyline and desipramine.

19. The composition of claim 14, and further comprising pharmaceutically acceptable viscosity agents, preservatives, buffers, and tonicity adjusting agents.

20. A composition for preventing irritation of a mucous membrane of the nose cause by allergies, chemical pollutants, or physical irritants manifested by sneezing, discomfort, stuffiness or mucous drainage as well as treating already irritated mucous membranes comprising a therapeutically effective amount of a tricyclic anti-depressant an effective amount of vasoconstrictor, and a flavoring agent wherein the tricyclic anti-depressant is selected from the group consisting of:

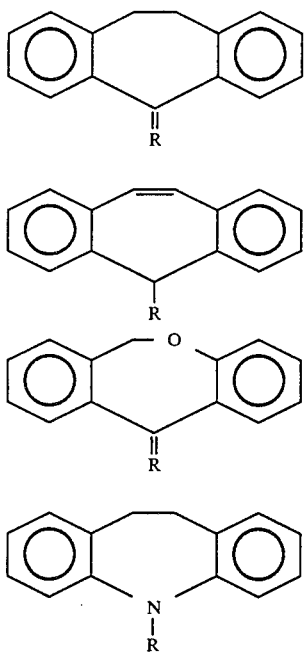

wherein R is an aliphatic secondary or tertiary amine connected to the ring by a three carbon chain in a suitable fluid carrier having an acceptable preservative and a buffering agent suitable to maintain the pH of said composition in the range of from about 3 to about 7, the topical application of said composition being suitable for application to a mucous membrane of the nose prophylactically preventing said irritation.

21. The composition of claim 20, wherein the tricyclic anti-depressant is selected from the group consisting of imipramine, amitriptyline, doxepin, notriptyline, protriptyline, desipramine and the acid addition salts thereof.

22. The composition of claim 20, wherein the tricyclic anti-depressant and the vasoconstrictor are present in an aqueous carrier, the concentration of the tricyclic anti-depressant in the carrier being not less than about 0.005% by weight of the carrier and the concentration of the vasoconstrictor in the carrier being not less than about 0.01% by weight of the carrier.

23. The composition of claim 22, wherein the anti-depressant is present in the range of between about 0.005% by weight and about 1.25% by weight of the carrier and the vasoconstrictor is present in the range of between about 0.01% by weight and about 1.0% by weight of the carrier.

24. The composition of claim 22, and further comprising a pharmaceutically acceptable viscosity adjusting agent, a preservative and a buffering agent, wherein said vasoconstrictor is selected from the group consisting of phenylephrine hydrochloride, tetrahydrozoline hydrochloride, xylometazoline hydrochloride, oxymetazoline hydrochloride, naphazoline hydrochloride, phenylephrine hydrochloride and ephedrine hydrochloride, the viscosity adjusting agent is selected from the group consisting of polyvinyl alcohol, methyl cellulose, hydroxymethyl cellulose, hydroxy propylmethyl cellulose, carboxymethyl cellulose and other soluble polymers, the preservative is selected from the group consisting of benzalkonium chloride, edetate disodium, sodium bisulfite, phenylmercuric acetate, cetylpyridinium chloride, thimerosal, chlorobutanol, cetyltrimethyl ammonium bromide, methylparaben, propylparaben and butylparaben and the buffering agent is selected from the group consisting of sodium phosphate monobasic, sodium phosphate dibasic, citric acid, sodium citrate, acetic acid, sodium acetate, boric acid, sodium carbonate, sodium borate, hydrochloric acid and sodium hydroxide.

* * * * *